United States Patent [19]

Brady

[11] Patent Number: 5,197,942
[45] Date of Patent: Mar. 30, 1993

[54] CUSTOMIZED FOOT ORTHOSIS

[76] Inventor: Harold Brady, 18429 Robson, Detroit, Mich. 48235

[21] Appl. No.: 819,864

[22] Filed: Jan. 13, 1992

[51] Int. Cl.$^5$ ............................. A61F 5/00; A61F 5/37
[52] U.S. Cl. ......................................... 602/5; 602/23; 128/882
[58] Field of Search .................. 602/23, 5, 27, 28, 29, 602/62; 128/882; 5/648-651; 36/71, 95, 110

[56] References Cited

U.S. PATENT DOCUMENTS

| | | | |
|---|---|---|---|
| 2,911,657 | 11/1959 | Streeter | 5/327 |
| 3,093,130 | 6/1963 | Cotton | 602/29 |
| 3,505,994 | 4/1970 | Smith | 5/648 |
| 3,511,233 | 5/1970 | Holy | 128/149 |
| 3,713,437 | 1/1973 | Wiedmer | 128/25 R |
| 3,859,740 | 1/1975 | Kemp | 36/71 |
| 4,076,022 | 2/1978 | Walker | 128/149 |
| 4,135,504 | 1/1979 | Spann | 5/648 |
| 4,186,738 | 2/1980 | Schleicher | 602/23 |
| 4,197,845 | 4/1980 | Browning | 128/149 |
| 4,641,639 | 2/1987 | Padilla | 602/23 |
| 4,693,239 | 9/1987 | Clover | 602/27 |
| 4,841,957 | 6/1989 | Wooten | 128/882 |
| 4,974,343 | 12/1990 | Davidson | 602/27 |
| 5,068,983 | 12/1991 | Marc | 36/71 |

OTHER PUBLICATIONS

"Foot Orthoses: Principles & Clinical Applications" by Kent K. Wu, pp. 249-279.

Primary Examiner—Robert A. Hafer
Assistant Examiner—Michael Brown
Attorney, Agent, or Firm—Krass & Young

[57] ABSTRACT

A customized foot orthosis designed to be worn by a patient having at least one ulcerated site on his or her foot. The foot orthosis comprises a brace having at least a back portion and a sole portion, an aperture extending through the sole portion, and means for fastening the orthosis securely to the patient's foot and lower leg. The aperture is positioned to correspond with the location of the ulcerated site on the patient's foot, thus relieving pressure from the ulcerated site when the patient is weight-bearing and thereby permitting the patient to be mobile while simultaneously assisting in the aeration and healing of the ulcerated site.

7 Claims, 2 Drawing Sheets

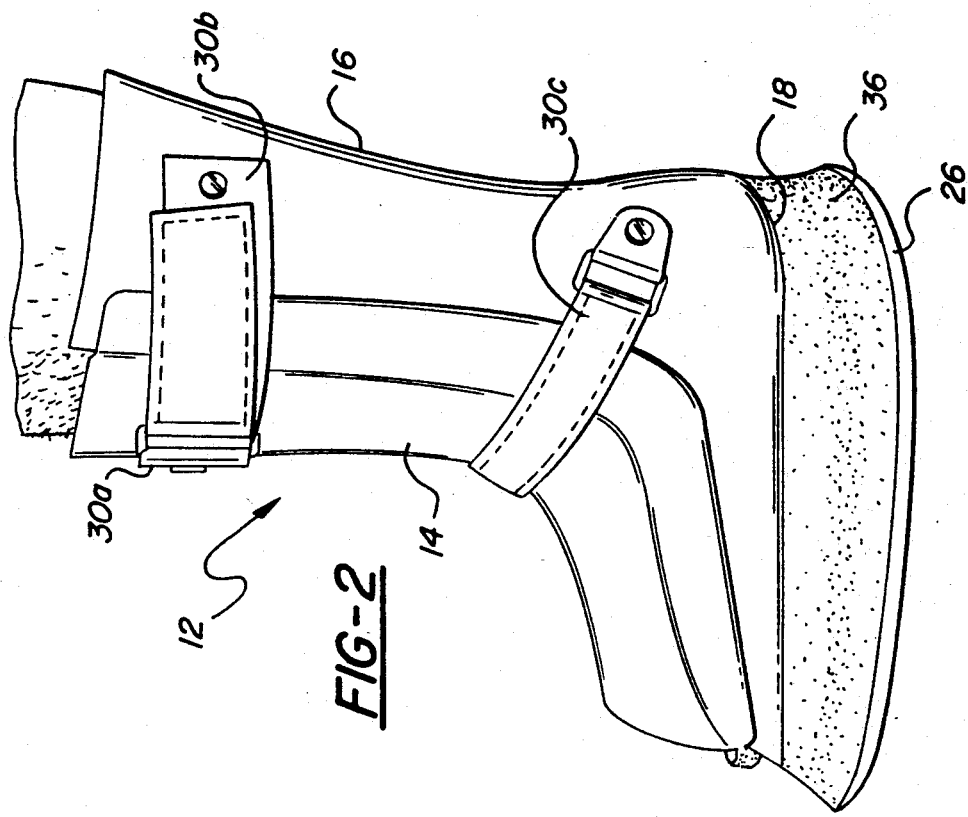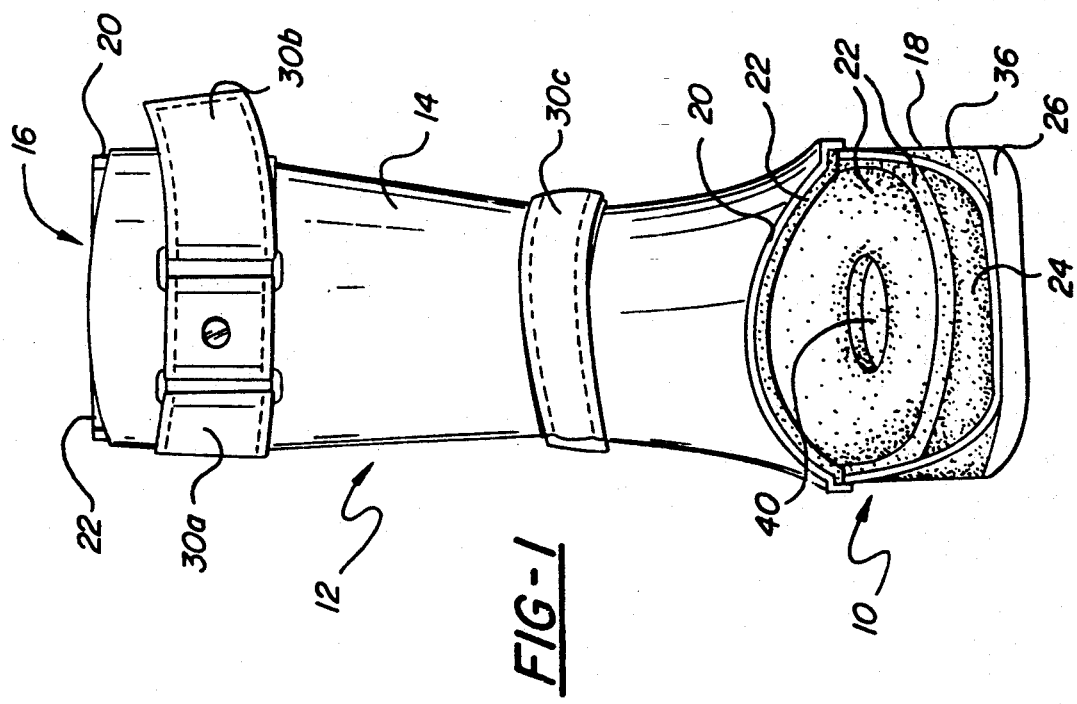

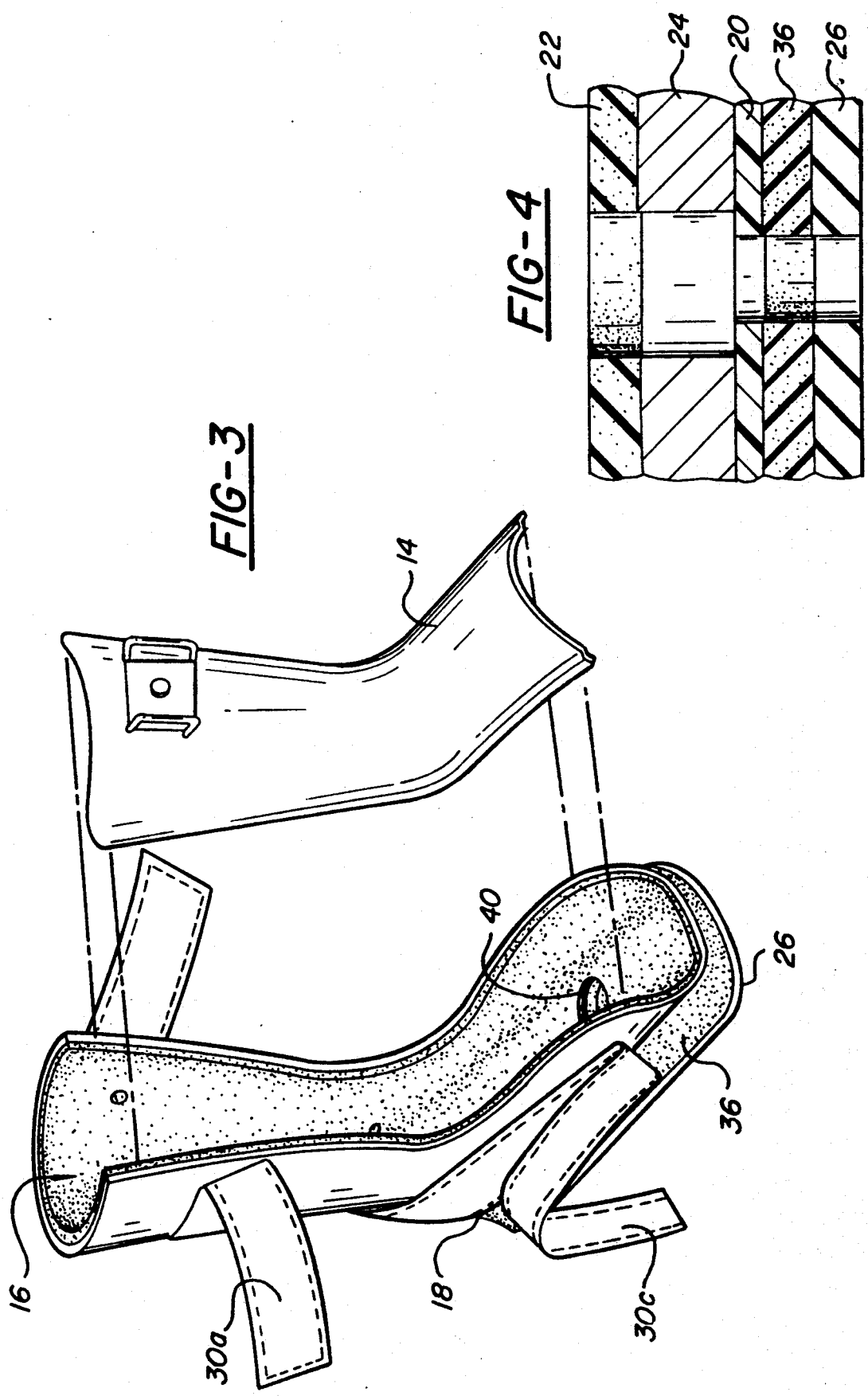

CUSTOMIZED FOOT ORTHOSIS

BACKGROUND OF THE INVENTION

1. Field of the Invention

This invention relates generally to the field of orthopedic appliances and more particularly to a customized foot orthosis which allows a patient to be mobile while simultaneously aerating and assisting in the healing of an ulcerated site on the patient's foot.

2. Description of the Related Prior Art

It is known in the prior art to provide a foot orthosis such as a support, brace, or protector to assist in the prevention of the formation of decubitus ulcers, commonly known as bed sores, on the heels of patients' feet. For example, the following patents all disclose devices specifically directed toward prevention and/or healing of a decubitus ulcer on the heel of the foot: U.S. Pat. No. 2,911,657 of Streeter, U.S. Pat. No. 3,511,233 of Holy, U.S. Pat. No. 4,076,022 of walker, and U.S. Pat. No. 4,197,845 of Browning.

The prior art devices do not prevent the occurrence of other types of ulcers in regions of the foot other than the heel. For example, it is not uncommon for diabetic ulcers to form on the sole of a diabetic patient's foot, often at the base of the toes. Unlike an ulcer on the heel, an ulcer on the sole of the foot prevents the patient from bearing weight on that foot and accordingly limits the patient's mobility. For this reason, in the past, patients with diabetic foot ulcers were treated with bed rest and confinement for a period of two to three months. Such bed rest severely debilitates the patient and disrupts his/her normal life. However, allowing the patient regular mobility could cause the ulcer to become infected, perhaps necessitating amputation.

Consequently, there is a need for an orthosis which accommodates ulcerated sites on the sole of a patient's foot and which allows the patient to engage in weight-bearing activities such as walking or standing, without aggravating or infecting the ulcerated site, while simultaneously aerating the ulcerated site, thus assisting in the healing process.

SUMMARY OF THE INVENTION

Disclosed and claimed herein is a customized foot orthosis designed to be used by patients having ulcerated sites on the soles of their feet. The foot orthosis comprises a brace, preferably constructed of rigid material, having a back portion and a sole portion with an aperture cut through the sole portion, and fastening means to secure the patient's foot and lower leg within the brace. Additional features of alternative embodiments include a brace having a front portion that is at least partially detachable from said back and sole portions of the brace; a flexible inner lining disposed within the brace; a sole cushion; and/or an outer sole to provide an anti-skid walking surface.

The position of the aperture corresponds with the position of an ulcerated site on the sole of a patient's foot when the patient is wearing the orthosis. The aperture in the orthosis permits the patient to be mobile and to bear weight on the foot: without aggravating the ulcerated site. At the same time, the aperture allows the ulcerated site to be aerated, thus assisting in the healing process. If the foot has a plurality of ulcerated sites, the foot orthosis may likewise include a corresponding plurality of apertures.

BRIEF DESCRIPTION OF THE DRAWINGS

Other objects and advantages of the invention will become apparent upon reading the following detailed description and upon reference to the drawings, in which:

FIG. 1 is a front elevational view of an embodiment of a customized foot orthosis constructed in accord with the teachings of the present invention;

FIG. 2 is a side elevational view of an embodiment of the present invention demonstrating how the patient's foot and lower leg is positioned within the invention;

FIG. 3 is a perspective view of an embodiment of the present invention with the front portion of the brace removed; and FIG. 4 is a cross-sectional view of the sole portion shown in FIG. 3 taken along lines 4—4 and showing an aperture extending through the sole.

DETAILED DESCRIPTION OF THE INVENTION

Referring now to the drawings and, in particular to FIGS. 1 and 2, there is depicted a foot orthosis 10 comprising a brace 12, having a back portion 16 and a sole portion 18, an aperture 40 extending through the sole portion 18 of the brace 12, and fastening means 30. Each foot orthosis 10 is custom-fitted for a patient having an ulcer on the sole of the foot; the aperture 40 is positioned to correspond with the ulcerated site on each individual patient's foot.

In the embodiment shown in both FIGS. 1 and 2, the brace 12 further comprises a front portion 14, in addition to the back portion 16 and the sole portion 18. As shown in FIG. 2, when the orthosis 10 is being worn by a patient, the front portion 14 covers the anterior aspect of the leg below the knee and the top of the patient's foot; the back portion 16 covers the posterior aspect of the patient's leg below the knee and extends to the back of the patient's heel; and the sole portion 18 covers the sole of the patient's foot.

In the preferred embodiment, each component of the brace 12, i.e. the front portion 14, the back portion 16, and the sole portion 18, has a rigid form-fitted outer shell 20 with a flexible inner lining 22 disposed therein. The rigid outer shell 20 is form-fitted for each individual patient to ensure a secure and comfortable fit of the foot orthosis 10. Preferably, the rigid outer shell 20 is constructed from fiberglass, but any similar material known in the art, such as plastic or plaster, may be used; the flexible inner lining 22 conforms to the shape of the shell 20 and is preferably made of a foam-like material, but other cushioning-type materials would be appropriate as well.

The inner lining 22 is designed to prevent any additional ulceration from occurring as a result of wearing the foot orthosis 10. As can most clearly be seen in FIG. 1, the thickness T of the inner lining 22 disposed adjacent the sole portion 18 of the brace 12 has a greater thickness than the thickness t of the lining 22 disposed adjacent the remainder of the brace 12. The additional thickness T of the lining 22 in the sole portion 1B is necessary to prevent the weight of the patient from compressing the inner lining 22 all the way down to the rigid outer shell 20 of the sole portion 18 of the brace 12 when the patient is standing or otherwise weight-bearing. Thus, in the preferred embodiment, the thickness T of the lining 22 in the sole portion 18 is approximately one inch whereas the thickness t of the lining 22 throughout the remainder of the brace 12 is approximately one quarter of an inch. As shown in FIG. 1, a sole cushion 24 may also be inserted between the inner lining 22 and the sole portion 18.

The orthosis of the present invention may further include an outer sole 26. Adhering means 36, such as hard molded foam, is disposed between the sole portion 18 of the brace 12 and the outer sole 26, thus bonding together the brace 12 and the outer sole 26. Other suitable adherents known in the art may also be used. The outer sole 26, which extends the entire length of the sole portion 18, acts as the walking surface of the orthosis 10. In the preferred embodiment, the bottom surface 27 of the outer sole 26 is shaped in a convex or "rocker bottom" fashion to assist the patient in simulating a normal walking gait. The outer sole 26 is preferably one quarter of an inch thick and is constructed from rubber. Other similar anti-skid materials may be equally appropriate for the outer sole 26.

An aperture 40, best seen in cross section in FIG. 4, is cut through the inner lining 22, and/or the sole cushion 24, the rigid outer surface 20 of the sole portion 18, the outer sole 26, and the adhering means 36 to relieve pressure from the ulcerated site when the patient is weight-bearing and to allow aeration of the ulcerated site. The exact position and shape of the aperture 40 varies from patient to patient depending upon the location and shape of the ulcerated site on the foot. The perimeter of the aperture 40 must be greater than the perimeter of the ulcer to ensure that pressure is eliminated from the area immediately surrounding the ulcer. If the foot has more than one ulcerated site, the foot orthosis 10 will include more than one aperture 40 to correspond with the requirements of each individual patient.

The perimeter of the aperture 40 may be uniform throughout or it may vary such that the perimeter of the aperture is greatest through the inner lining 22 and smallest through the outer sole 26. In the preferred embodiment including a sole cushion 24 illustrated in FIG. 4, the perimeter of the aperture 40 has a stair-step configuration. The perimeter of the aperture 40 extending through the inner lining 22 is approximately equal to the perimeter of the aperture 40 extending through the sole cushion 24; similarly, the perimeters of the aperture 40 extending through the rigid outer surface 20 of the sole portion 18, the adhering means 36, and the outer sole 26 are approximately equal to each other, but less than the perimeters of the aperture 40 extending through the inner lining 22 and the sole cushion 24. When viewed in cross-section as shown in FIG. 4, the perimeter of the aperture 40 resembles a stair step. When a patient wearing a foot orthosis 10 having a stair-step aperture 40 takes a step, air is pumped up the aperture 40 toward the ulcerated site. In this manner, the foot orthosis 10 provides improved aeration of the ulcerated site and promotes the healing thereof.

In order to permit the comfortable insertion of the patient's foot and leg into the orthosis 10 in embodiments including the front portion 14, the front portion 14 is at least partially detachable from the back portion 16 and the sole portion 18. Likewise, this feature makes the removal of the foot orthosis 10 an easy task that the patient can perform independently. Thus, the foot orthosis 10 may be easily removed for the comfort and convenience of the patient when the patient is engaging in non-weight-bearing activities such as sleeping or bathing.

FIG. 3 illustrates a preferred embodiment of the present invention wherein the back portion 16 and the sole portion 18 of the brace 12 are integrally formed together and the front portion 14 of the brace 12 is completely detachable. Fastening means 30 securely holds the front portion 14 of the brace 12 to the orthosis 10 so that the patient's ankle joint is immobilized, and the patient's leg and foot is held securely in position within the orthosis 10 to prevent the sole of the foot from slipping or shifting and to transfer some of the pressure from the sole of the foot to the lower leg during weight-bearing activities. The number and the positioning of the fastening means 30 required may vary depending on the individual patient; however, so long as complete immobilization of the foot within the foot orthosis 10 is achieved, the fastening means 30 effectively serve their purpose. Complete immobilization is imperative; otherwise, the ulcerated site may move away from the aperture 40, thus hindering the healing process and possibly leading to infection and subsequent amputation of the patient's foot.

In the preferred embodiment, three Velcro® straps 30a,30b,30c mounted on the back portion 16 of the brace 12 function as the fastening means 30 in conjunction with corresponding buckles 30d,30e,30f. Two straps 30a,30b are mounted opposite one another near the top of the back portion 16; corresponding buckles 30d,30e are mounted on the front portion 14. A third strap 30c is mounted near the bottom of the back portion 16 near the ankle bone; a corresponding buckle 30f (best seen in FIG. 2) is mounted on the opposite side of the back portion across from the third strap 30c. When the front portion 14 is positioned upon the back and sole portions 16,18 of the brace 12, the straps 30a,30b,30c are looped through the corresponding buckles 30d,30e,30f and are tightened as shown in FIGS. 1 and 2. Snaps or other appropriate fastening means may also be used.

Thus it is apparent that there has been provided, in accordance with the invention, a customized foot orthosis 10 which simultaneously assists in the healing process of an ulcerated site on the sole of a patient's foot while allowing the patient to engage in weight-bearing activities. While the invention has been described in conjunction with specific embodiments thereof, it is evident that many alternatives, modifications, and variations will be apparent to those skilled in the art in light of the foregoing description. Accordingly, the present invention embraces all such alternatives, modifications, and variations as falling within the spirit and broad scope of the claims.

I therefore claim:

1. A customized foot orthosis to assist in the healing of an ulcerated site located on the sole of a patient's foot, said orthosis comprising:

an individually-fitted one-piece brace having a back portion and a sole portion, the back portion of said brace extending form the posterior aspect of the patient's leg below the knee to the back of the patient's heel, and the sole portion of said brace covering the sole of the patient's foot;

a flexible inner lining disposed within and conforming to said brace;

fastening means to securely hold the patient's leg and foot within said brace; and an aperture including a first portion extending through the sole portion of said brace, and a second portion extending through said lining, the perimeter of said second portion of said aperture being greater than the perimeter of the ulcerated site, said aperture being positioned to correspond to the location of the ulcerated site when the patient's foot and leg are securely positioned within said orthosis, whereby the aperture in the sole portion of the orthosis permits the patient to walk and engage in other weight-bearing activities without applying pressure to the ulcerated site and also aerates the ulcerated site, thus promoting healing thereof.

2. The foot orthosis of claim 1 further comprising an outer sole secured to and disposed beneath said sole portion of said brace, said outer sole extending the entire length of said portion and functioning as a walking surface.

3. The foot orthosis of claim 2 wherein said outer sole includes a bottom surface which is convex-shaped to assist the patient in simulating a normal walking gait.

4. The foot orthosis f claim 2 wherein the aperture further included a third portion which extends through the outer sole, said third portion having a perimeter which is smaller than the perimeter of the second portion of the aperture extending through the inner lining.

5. The foot orthosis of claim 1 wherein said brace comprises a front portion configured to engage the back and sole portions of said brace, said front portion being at least partially detachable from said back and sole portions and covering the anterior aspect of the leg and the top of the foot.

6. The foot orthosis of claim 1 wherein the brace is rigid.

7. A customized foot orthosis to assist in the healing of an ulcerated site located on the sole of a patient's foot, said orthosis comprising:
- a rigid, individually-fitted brace having a back portion and a sole portion, the back portion of said brace extending from the posterior aspect of the patient's leg below the knee to the back of the patient's heel, and the sole portion of said brace covering the sole of the patient's foot, said brace further comprising a front portion configured to engage the back and sole portions of said brace, said front portion being at least partially detachable from said back and sole portions and covering the anterior aspect of the leg and the top of the foot;
- a flexible inner lining disposed within said brace and conformable thereto, said lining having a thickness in a first portion thereof adjacent the sole portion of said brace that is greater than the thickness of a second portion adjacent the front and back portions of said brace;
- means to fasten the front portion to the back and sole portions of said brace to securely hold the patient's leg and foot within said brace;
- an outer sole secured to and disposed beneath said sole portion of said brace, said outer sole extending the entire length of said sole portion and functioning as a walking surface; and
- an aperture having a first portion extending through the inner lining of the sole portion, a second portion extending through the sole portion of the brace, and a third portion extending through the outer sole, said first portion having a perimeter greater than the perimeter of the ulcerated site, the perimeter of said second portion, and the perimeter of the third portion, said aperture being positioned to correspond to the location of the ulcerated site when said foot is inside said orthosis, whereby the aperture in the orthosis permits the patient to walk and engage in other weight-bearing activities without applying pressure to the ulcerated site and also aerates the ulcerated site, thus promoting healing.

* * * * *

UNITED STATES PATENT AND TRADEMARK OFFICE
CERTIFICATE OF CORRECTION

PATENT NO. : 5,197,942

DATED : March 30, 1993

INVENTOR(S) : Harold L. Brady

It is certified that error appears in the above-identified patent and that said Letters Patent is hereby corrected as shown below:

Column 1, Line 21, Delete "walker" Insert --Walker--

Column 1, Line 63, Delete "foot: without" Insert --foot without--

Column 2, Line 61, Delete "1B" Insert --18--

Column 4, Line 57, Delete "form" Insert --from--

Column 5, Line 14, Delete "said portion" Insert --said sole portion--

Column 5, Line 19, Delete "f" Insert --of--

Drawings Insert --T/t-- in Figure 1

Signed and Sealed this

Twenty-second Day of March, 1994

*Attest:*

BRUCE LEHMAN

*Attesting Officer*     *Commissioner of Patents and Trademarks*